(12) United States Patent
Gangadharan

(10) Patent No.: US 10,533,281 B2
(45) Date of Patent: Jan. 14, 2020

(54) METHOD FOR SEPARATING AND BREAKING DOWN BIODEGRADABLE AND NON-BIODEGRADABLE MATERIALS

(71) Applicant: Anand Gangadharan, Novi, MI (US)

(72) Inventor: Anand Gangadharan, Novi, MI (US)

( * ) Notice: Subject to any disclaimer, the term of this patent is extended or adjusted under 35 U.S.C. 154(b) by 0 days.

(21) Appl. No.: 15/337,000

(22) Filed: Oct. 28, 2016

(65) Prior Publication Data

US 2017/0121905 A1 May 4, 2017

Related U.S. Application Data

(60) Provisional application No. 62/247,933, filed on Oct. 29, 2015.

(51) Int. Cl.
| | | |
|---|---|---|
| *D21B 1/10* | (2006.01) | |
| *D21B 1/06* | (2006.01) | |
| *C12P 5/02* | (2006.01) | |

(52) U.S. Cl.
CPC ............. *D21B 1/10* (2013.01); *D21B 1/06* (2013.01); *C12P 5/023* (2013.01)

(58) Field of Classification Search
CPC ............. D21B 1/10; D21B 1/06; C12P 5/023
USPC ........................................................ 435/167
See application file for complete search history.

(56) References Cited

U.S. PATENT DOCUMENTS

| | | |
|---|---|---|
| 5,635,394 A | 6/1997 | Horn |
| 6,337,203 B1 | 1/2002 | Beaulieu |
| 7,955,839 B2 | 6/2011 | Choate et al. |
| 2012/0067293 A1 | 3/2012 | Treloar et al. |

FOREIGN PATENT DOCUMENTS

EP 2826543 * 1/2015 ............. B01D 53/44

OTHER PUBLICATIONS

Quincy Park Recycling Drop-Off Center, Trash & Recycling, Arlington, VA, Available Online at: recycling.arlingtonva.us/locations/quincy-park-recycling-drop-off-center/, Accessed Nov. 17, 2017.*
Chen et al., Mitigating Odors from Agricultural Facilities: A Review of Literature Concerning Biofilters, Applied Engineering in Agriculture, vol. 25(5) (2009) pp. 751-766.*

* cited by examiner

*Primary Examiner* — Jennifer M. H. Tichy
(74) *Attorney, Agent, or Firm* — William H. Honaker; Dickinson Wright PLLC

(57) ABSTRACT

A method for breaking down a pallet of plastic, paper, cardboard, and organic material to produce bio-gas, fertilizer, and water includes a step of maintaining a negative pressure during the steps of removing, separating, recycling, feeding, and converting to clean odorous air. The step of maintaining the negative pressure is further defined as removing the odorous air generated during the steps of separating, recycling, feeding, and converting. The chamber of the biofilter is maintained at a predetermined humidity of at least 80% and a predetermined temperature of between 70° F. and 80° F. A biofilter for removing odorous air includes a filter media having a mixture of woodchips having hardwood chips being present between 30 wt. % and 50 wt. %, softwood chips being present between 50 wt. % and 70 wt. %, and microorganisms disposed therein.

2 Claims, 7 Drawing Sheets

METHOD FOR SEPARATING AND BREAKING DOWN BIODEGRADABLE AND NON-BIODEGRADABLE MATERIALS

CROSS REFERENCE TO RELATED APPLICATION

This application claims the benefit of a provisional application Ser. No. 62/247,933 filed on Oct. 29, 2015.

BACKGROUND OF THE INVENTION

1. Field of the Invention

The present invention generally relates a biofilter for removing odorous air and a method for breaking down a pallet including plastic, paper, cardboard, and organic material to produce bio-gas, fertilizer, and water and removing odorous air generated during the production of the bio-gas, fertilizer, and water.

2. Description of the Prior Art

Traditional method of waste handing has been landfilling—a process of burying waste in a landfill. However, landfilling can cause environmental pollution discharges to the water and, as real estate values increase, is considered to be an unattractive use of land. Thus, current waste management strategies seek to limit the amount of refuse directed to landfills. Recycling and composting programs have become widely accepted for both commercial and residential waste to reduce the demands on landfills.

Anaerobic digestion presents an alternative for handling organic waste materials. The primary object of anaerobic digestion is the production of a mixture of bio-gas, which may be utilized as an energy source to generate electricity and/or heat. Any solid material remaining at the end of the anaerobic digestion process is typically disposed of by conventional landfilling or composted into soil amendment. Typically, plastic, paper, cardboard, and other non-organic material cannot be accepted into an anaerobic waste processing facility.

On such method is disclosed in U.S. Pat. No. 7,955,839. The method issued for breaking down a pallet including plastic, paper, cardboard, and organic material to extract organic material to feed into an anaerobic digester to produce bio-gas, e.g. bio-methane. The first step of the method is removing the cardboard, e.g. packaging material, from the paper and/or the plastic and the organic material. The next step of the method is separating the organic material from the paper and the plastic, e.g. plastic containers. The organic material is then fed to the anaerobic digester. Finally, the organic material is converted to the bio-gas, the fertilizer, and the water using the anaerobic digester. The paper and the plastic may be recycled One such biofilter is disclosed in U.S. Pat. No. 6,337,203. The biofilter includes a housing having a top wall and a bottom wall. Side walls extends between the top wall and the bottom wall connecting the top wall with the bottom wall and defining chamber between the top wall the bottom wall and the side walls. The bottom wall of the housing defines at least one entrance disposed in communication with the chamber for transferring the odorous air into the chamber. A plurality of trays disposed in the chamber and attached to the housing. A filter media is disposed on each of the trays for removing odor from the odorous air in the chamber and produce a purified air. At least one sprinklers disposed in the chamber and attached to the housing for transferring water into the chamber of the housing to maintain the chamber of the housing in a predetermined humidity. A heater disposed in the housing of the chamber and attached to the top wall of the housing to maintain the chamber of the housing between a predetermined temperature. The top wall of the housing defines an exit disposed adjacent to the side wall of the housing for removing the purified air from the chamber of the housing.

SUMMARY OF THE INVENTION

It is one aspect of the invention to provide for a method for breaking down a pallet including plastic, paper, cardboard, and organic material to produce bio-gas, e.g. bio-methane, fertilizer, and water. The method uses an anaerobic digester and a biofilter. The biofilter has a housing defining a chamber, the housing having at least one entrance, a drain, at least one sprinkler, a heater, and a plurality of trays that include a filter media. The first step of the method is removing the cardboard from the paper, the plastic, and the organic material. The next step of the method is separating the organic material from the paper and the plastic. After separating the organic material from the paper and the plastic, the paper and the plastic are recycled. Next, the organic material is fed to the anaerobic digester. Using the anaerobic digester, the organic material is converted to the bio-gas (sometimes referred to as bio-methane), the fertilizer, and the water using the anaerobic digester. During the steps of removing, separating, recycling, feeding, and converting, a negative pressure is maintained to retain odorous air generated during the steps of removing, separating, recycling, feeding, and converting.

It is another aspect of the present invention to provide a biofilter for removing odorous air. The biofilter includes a housing having a top wall, a bottom wall and side walls. The side walls extends between the top wall and the bottom wall connecting the top wall and the bottom wall defining chamber between the top wall, the bottom wall, and the side walls. The bottom wall of the housing defines at least one entrance disposed in communication with the chamber for transferring the odorous air into the chamber. A plurality of trays is disposed in the chamber and attached to the housing. A filter media is disposed on each of said trays for removing odor from the odorous air in the chamber and produce a purified air. At least one sprinkler is disposed in the chamber and attached to the housing for transferring water into the chamber of the housing to maintain the chamber of said housing in a predetermined humidity. A heater is disposed in the housing of the chamber and attached to the top wall of the housing to maintain the chamber of the housing at a predetermined temperature. The top wall of the housing defines an exit disposed adjacent to the side wall of the housing for removing the purified air from the chamber of the housing. The filter media includes a mixture of woodchips including a plurality of hardwood chips being present between 30 wt. % and 50 wt. % and a plurality of softwood chips being present between 50 wt. % and 70 wt. %.

The present invention in its broadest aspect provides for a high efficiency recycling process. In addition, the present invention provides for a recycling process that has produces minimal environmental pollution effects to its surroundings.

BRIEF DESCRIPTION OF THE DRAWINGS

Other advantages of the present invention will be readily appreciated, as the same becomes better understood by reference to the following detailed description when considered in connection with the accompanying drawings wherein.

DESCRIPTION OF THE ENABLING EMBODIMENT

Figure 1:
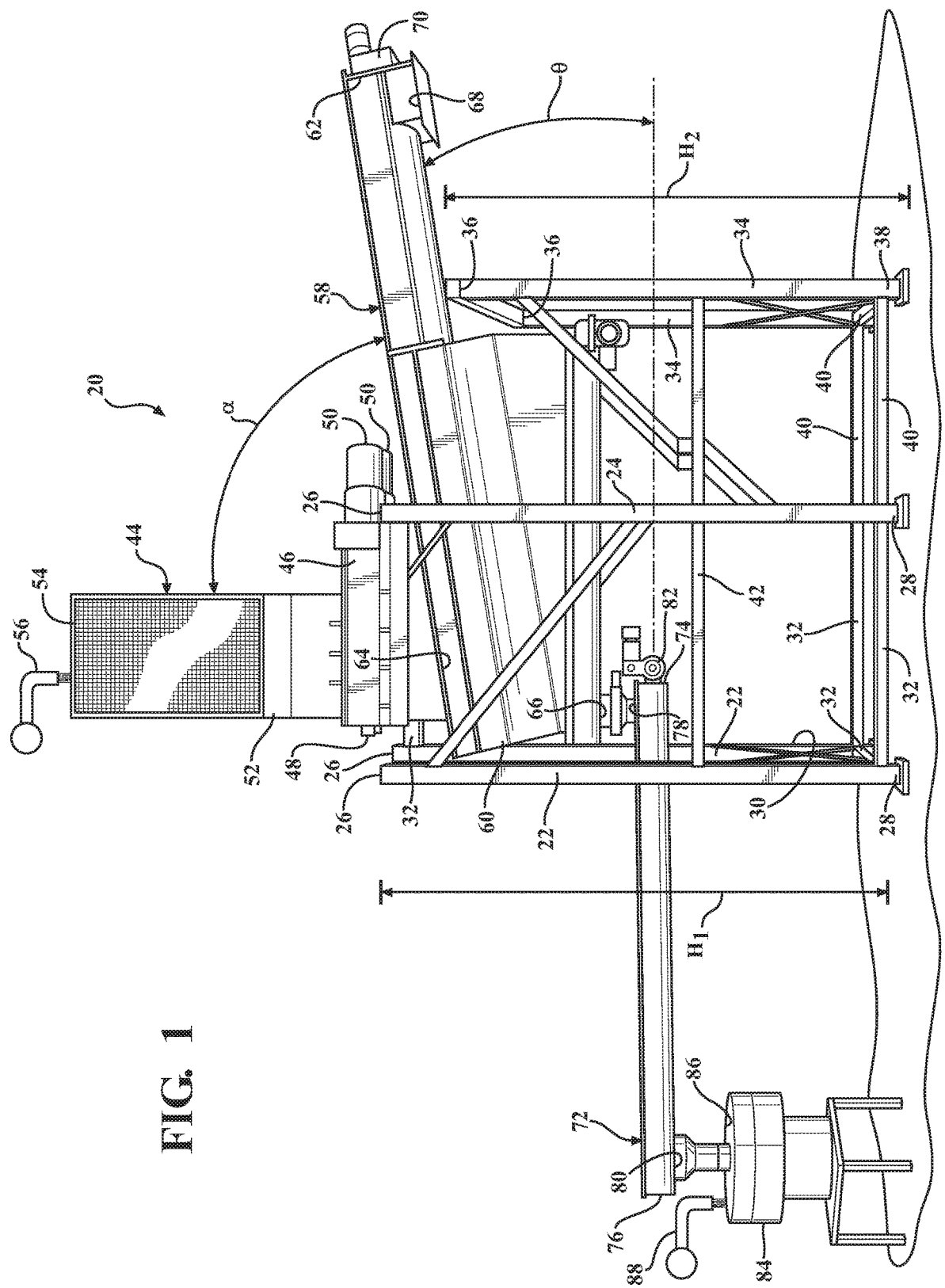
FIG. 1 is a perspective side view of the apparatus.
Figure 2:
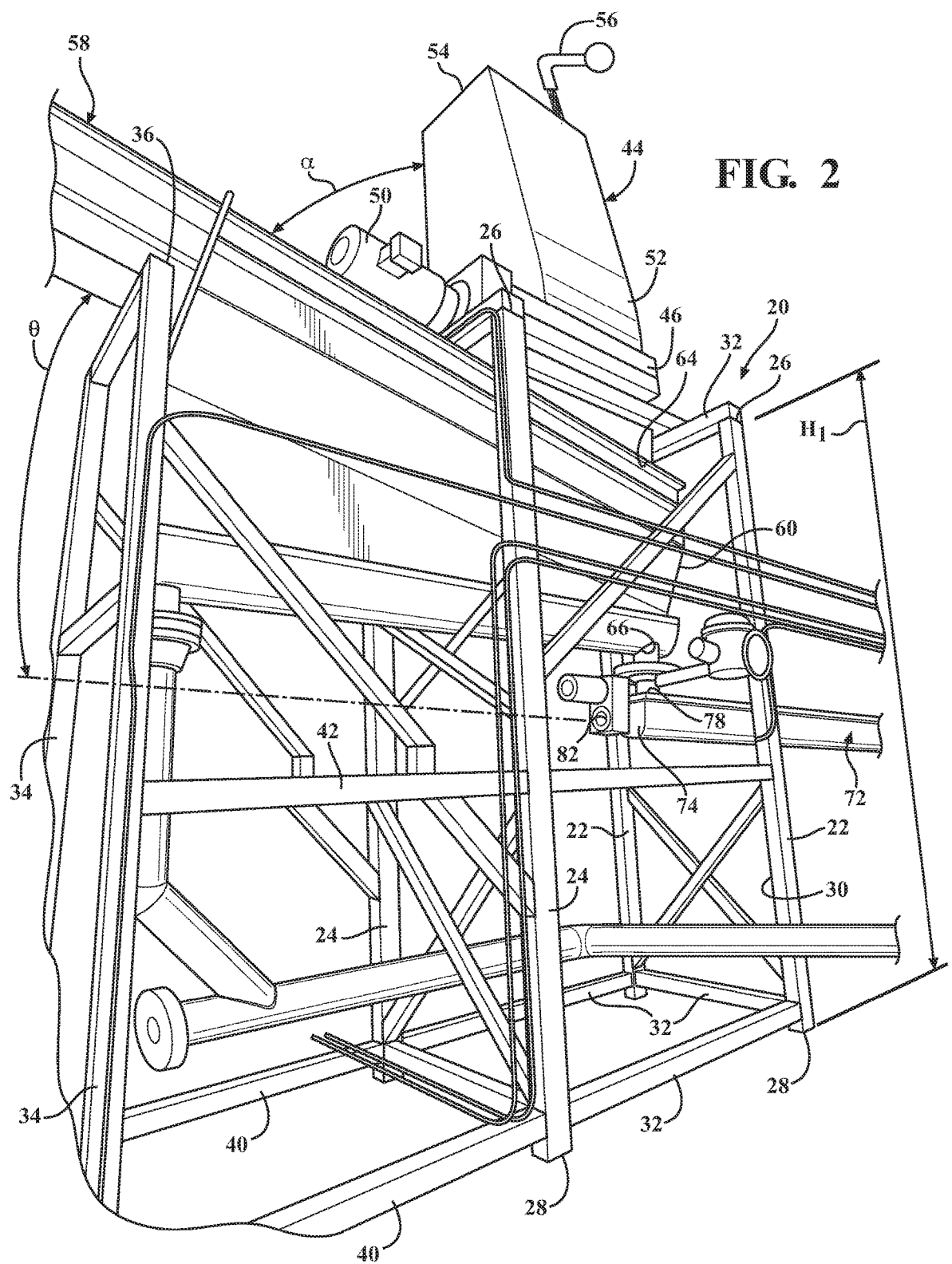
FIG. 2 is a fragmentary enlarged view of the apparatus.

Referring to the Figures, wherein like numerals indicate corresponding parts throughout the several views, an apparatus for separating and recycling a pallet including plastic, paper, cardboard, and organic material is generally shown in FIG. 1.

The apparatus includes a frame 20 having a rectangular shape. The frame 20 includes a plurality of four poles 22, 24 each having a rectangular shaped cross-section. Alternatively, instead of rectangular shaped, the poles 22, 24 may have a different shaped cross-section such as, but not limited to circular shaped. The poles 22, 24 are disposed parallel and spaced from one another. The poles 22, 24 also extend between a first end 26 and a second end 28 to define a first predetermined height $H_1$ between the first end 26 and the second end 28. The poles 22, 24 include a first pair of two poles 22 disposed parallel and spaced from one another and a second pair of two poles 24 disposed adjacent and spaced from the first pair of two poles 22 parallel to the first pair of two poles 22 and defining a compartment 30 having a rectangular shape extending between the first pair of two poles 22 and the second pair of two poles 24. In other words, the first pair of two poles 22 and the second pair of two poles 24 are arranged in a rectangular shaped configuration to define a compartment 30 extending there between.

The frame 20 also includes a plurality of beams 32 each having a rectangular shaped in cross-section and disposed at the first end 26 and the second end 28 of the poles 22, 24. Alternatively, instead of rectangular shaped, the beams 32 may have a different shaped cross-section such as, but not limited to circular shaped. The beams 32 extend perpendicularly between the poles 22, 24 connecting the poles 22, 24 to one another. The frame 20 further includes a pair of support members 34. Each of the support members 34 may have a rectangular shaped cross-section. Alternatively, instead of rectangular shaped the support members 34 may have a different shaped cross-section such as, but not limited to circular shaped. The support members 34 are disposed spaced from one another and adjacent and parallel to the second pair of two poles 24. The support members 34 extend between a third end 36 disposed adjacent to the first end 26 and a fourth end 38 disposed adjacent to the second end 28 of the poles 22, 24 to define a second predetermined height $H_2$ between the third end 36 and the fourth end 38. The second predetermined height $H_2$ is less than the first predetermined height $H_1$. A plurality of rails 40, each having a rectangular shaped cross-section, is disposed at the fourth end 38 of the support members 34 and extends perpendicularly between the support members 34 and the second pair of two poles 24 and the support members 34. The rails 40 connect the support members 34 to one another and the second pair of two poles 24 to the support members 34. The frame 20 further includes a plurality of two bars 42, each having a rectangular shaped cross-section, disposed spaced and parallel to one another between the beams 32 and the rails 40. Each of the bars 42 extends perpendicularly from the first pair of two poles 22 to the support members 34 connecting the poles 22, 24 to the support members 34.

A shredder 44 is disposed adjacent to the first end 26 of the poles 22, 24 and attached to the beams 32 of the frame 20 for breaking the organic material and the paper and the plastic into smaller pieces. The shredder 44 includes a cover 46 attached to the beams 32 of the frame 20. A plurality of shafts 48, disposed in a parallel relationship with the beams 32 of the frame 20 and to one another, each of the shafts 48 extends transversely through the cover 46 for engaging the organic material and the paper and the plastic from the pallet. The shredder 44 further includes a motor 50, disposed adjacent to the second pair of poles 22, 24, attached to the cover 46 and coupled to the shafts 48 to rotate each of the shafts 48. The shredder 44 further includes a container 52 having a rectangular shape in cross-section, disposed in communication with the cover 46, extends perpendicularly outwardly from the cover 46 and away from the frame 20 to an open end 54 for receiving the organic material and the paper and the plastic. A nozzle 56 is attached to the open end 54 of the container 52 for adding water into the shredder 44 to wash the paper and the plastic in the container 52 to remove the organic material from the paper and the plastic.

A carrier 58 is disposed in the compartment 30 of the frame 20 and extends between a proximate end 60 disposed adjacent to the shredder 44 and a distal end 62 bolstered by the third end 36 of the support members 34 and attached to the frame 20. The carrier 58 defines an inlet 64 disposed adjacent to the proximate end 60, in communication with the shredder 44, for receiving the smaller pieces of the organic material, the paper, and the plastic from the shredder 44. The carrier 58 also defines an opening 66 disposed adjacent to the proximate end 60 of the carrier 58 and spaced from the inlet 64 for discharging the organic material from the carrier 58. The carrier 58 further defines an outlet 68 disposed adjacent to the distal end 62 of the carrier 58 for discharging the plastic and the paper from the carrier 58. The carrier 58 includes a conveyor 70 of mesh material extending between the proximate end 60 and the distal end 62 of the carrier 58 for transferring the plastic and the paper from the inlet 64 of the carrier 58 to the outlet 68 of the carrier 58 to a compactor for recycling.

A transport 72 having a tubular shape is disposed in the compartment 30 of the frame 20 and attached the frame 20 adjacent to the carrier 58 and extending from a primary end 74 disposed adjacent to the carrier 58 and perpendicular to the first pair of two poles 22 to a secondary end 76 spaced from the first pair two poles 22, 24. The transport 72 defines a first orifice 78 disposed at the primary end 74 of the transport 72 and in communication with the opening 66 of the carrier 58 for receiving the organic material from the carrier 58 and a second orifice 80 disposed at the secondary end 76 of the transport 72 for discharging the organic material from the transport 72. The transport 72 further includes an auger 82 disposed in the transport 72 and extending transversely between the primary end 74 and the secondary end 76 of the transport 72 for delivering the organic material from the primary end 74 of the transport 72 to the secondary end 76 of the transport 72.

A separator 84 is disposed adjacent to the second orifice 80 of the transport 72. The separator 84 defines a bore 86 disposed in communication with the second orifice 80 of the transport 72 for receiving the organic material from the carrier 58. The separator 84 includes a screen of ⅛" meshed wires movably, by vibration, disposed in the separator 84 for further removing the paper and the plastic from the organic material. The separator 84 further includes an injector 88 for adding water into the separator 84 for washing the screen to remove the organic material from the screen and the paper and the plastic.

The carrier 58 is disposed at a first predetermined angle α of less than 90°, preferably 60°, relative to the shredder 44 for allowing the organic material to flow toward the proximate end 60 of the carrier 58. The transport 72 being disposed at a second predetermined angle θ of less than 90°, preferably 30°, relative to the carrier 58 with a sum of the first predetermined angle α and the second predetermined angle θ being equal to 90°.

Figure 3:
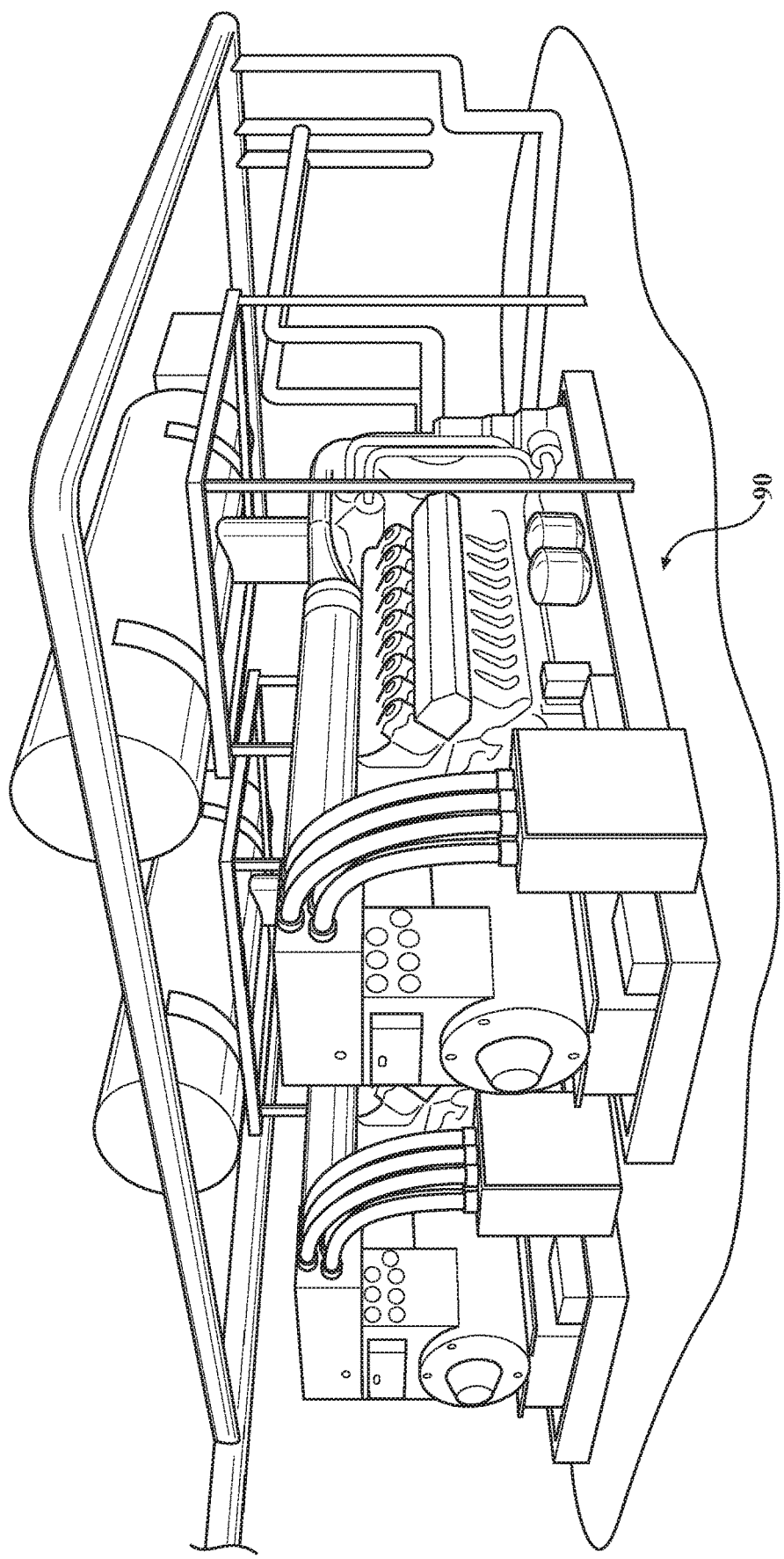
FIG. 3 is a perspective view of a plurality of engines for receiving the bio-gas produced by converting the organic material.

In operation, a pallet including plastic, paper, cardboard, and organic material is first delivered to an anaerobic digester facility. The cardboard is first removed from the pallet. The cardboard may be removed either manually or by a cardboard remover device (not shown). Next, the organic material, the paper, and the plastic, are fed, via delivery device such as a conveyor 70 belt (not shown), through the open end 54 of the container 52 of the shredder 44. The shafts 48 of the shredder 44, powered by the motor 50, rotate in the shredder 44 to break the organic material, the paper, and the plastic in to smaller pieces. At the same time, water may be added to wash the organic material, and the plastic in the container 52, to remove the organic material from the paper and the plastic. The smaller pieces of the paper, the plastic, and the organic material are then received by the carrier 58, through the inlet 64 of the carrier 58, including the conveyor 70. The organic material flows through the carrier 58 and the smaller pieces of the paper and the plastic are transferred from the inlet 64 of the carrier 58 to the outlet 68 at the distal end 62 of the carrier 58. A compactor may be disposed near the outlet 68 of the carrier 58 for receiving and recycling the paper and plastic. The carrier 58 is positioned at an acute angle relative to the shredder 44 such that, as the paper and the plastic are transferred from the inlet 64 to the outlet 68, any remaining organic material flows toward the opening 66 near the proximate end 60 of the carrier 58. The organic material is then fed into the separator 84 using the transport 72. The organic material is then filtered using the separator 84. The separator 84 is made from ⅛" meshed wires. The separator 84 may be vibrated to facilitate with the filtration process. From the separator 84, the organic material is sent for further processing in an anaerobic digester to convert the organic material into bio-gas, fertilizer, and water. Alternatively, the anaerobic digester may be directly attached to the secondary end 76 of the transport 72 to directly receive the organic material to convert the organic material into bio-gas, fertilizer, and water. The water produced by the anaerobic digester may be discharged directly into the local stream or sewage. The bio-gas produced by the anaerobic digester may be fed directly to an engine 90 or a plurality of engines 90, as generally shown in FIG. 3, to generate power and provide thermal energy. The fertilizer produced by the anaerobic digester may be used directly on plants.

Figure 4:
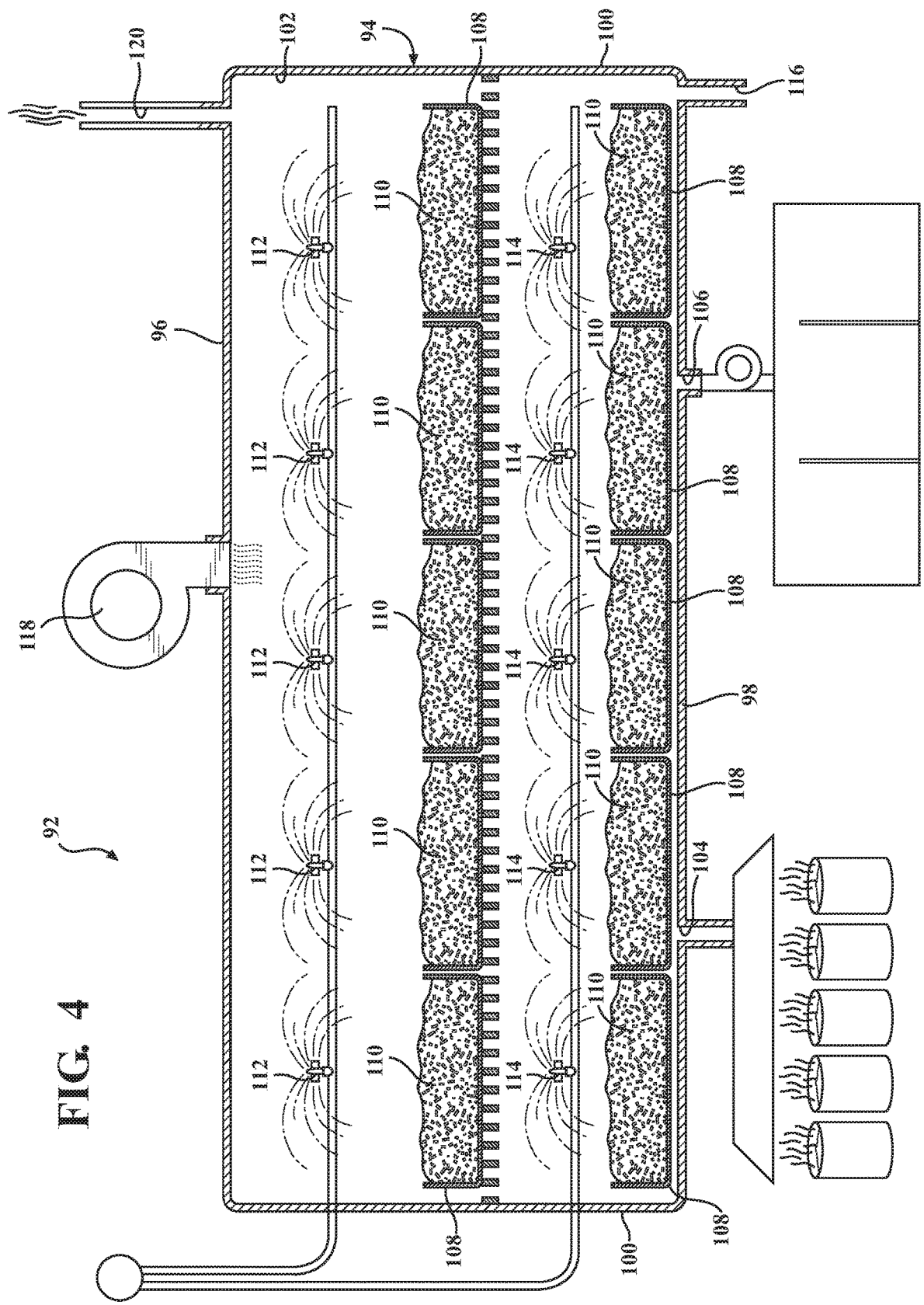
FIG. 4 is a cross-sectional view of the biofilter.
Figure 5:
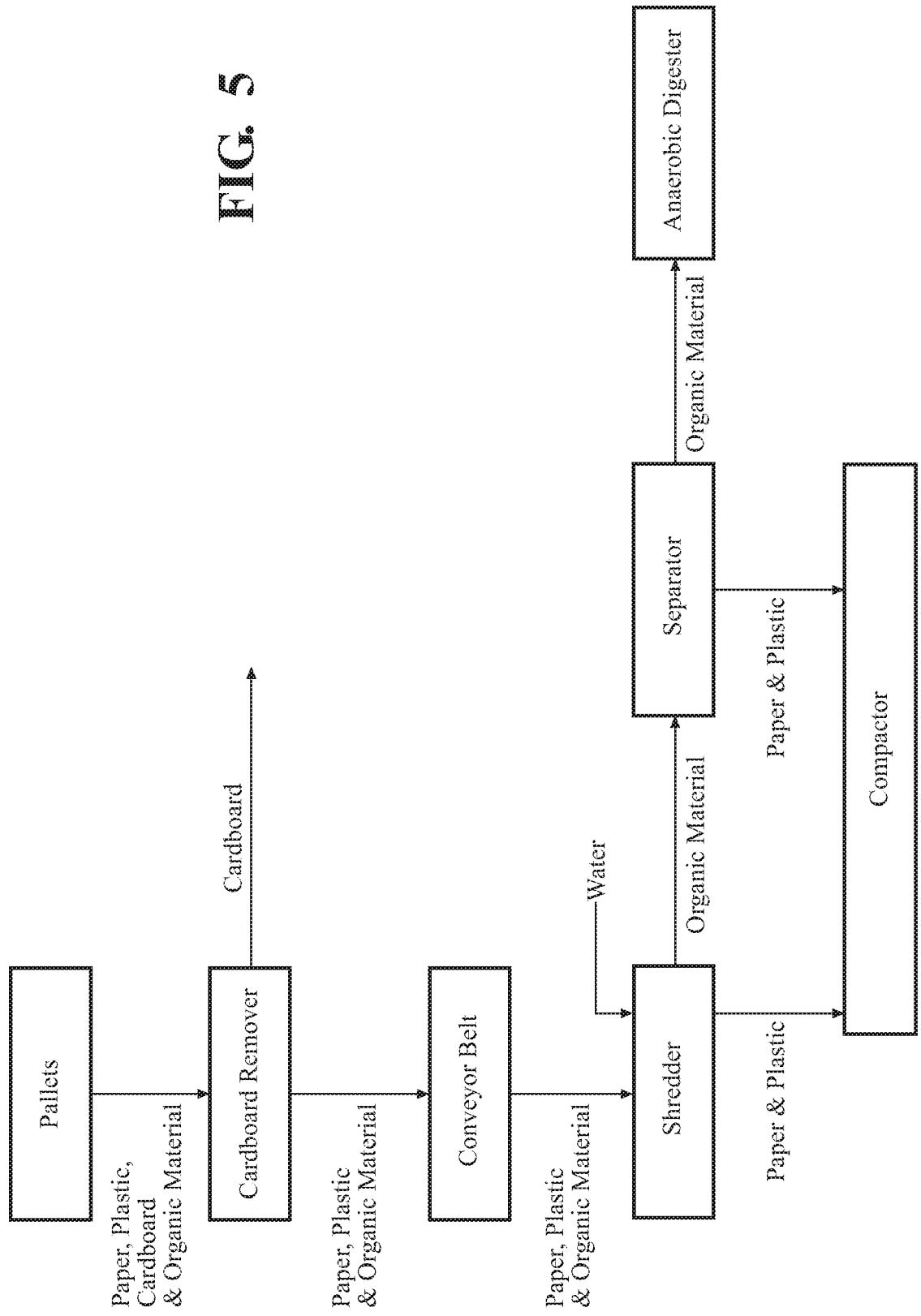
FIG. 5 is a schematic view of the method for breaking down a pallet including plastic, paper, cardboard, and organic material.

It is one aspect of the present invention to provide a biofilter 92 for removing odorous air generated in an anaerobic digester plant. The odorous air from various areas of the anaerobic digester plant is evacuated through the biofilter 92 to remove odor before air is released. The biofilter 92, as generally shown in FIG. 4, includes a housing 94 having a rectangular shape in cross-section. The housing 94 includes a top wall 96 and a bottom wall 98 disposed parallel and spaced from one another. The housing 94 further includes side walls 100 extending perpendicularly between the top wall 96 and the bottom wall 98 connecting the top wall 96 with the bottom wall 98 and defining a chamber 102 extending between the top wall 96, the bottom wall 98, and the side walls 100. The bottom wall 98 of the housing 94 defines at least one entrance 104, 106. The at least one entrance 104, 106 may include a first entrance 104 and a second entrance 106. The first entrance 104 is disposed in communication with a plurality of air tanks for transferring the odorous air from the air tanks to the chamber 102 of the housing 94. The second entrance 106 is spaced from the first entrance 104 and is in communication with specific rooms at a negative pressure for transferring the odorous air from the specific rooms to the chamber 102 of the housing 94. The transferring of the odorous air from the specific rooms and the air tanks to the chamber 102 can be performed by using a fan or a pump.

A plurality of trays 108 is disposed in the chamber 102 of the housing 94, spaced from one another, and attached to the housing 94. A filter media 110 of a mixture of woodchips is disposed in each of the trays 108 for removing odor from the odorous air in the chamber 102 to produce purified air. At least one sprinkler 112, 114, disposed in the chamber 102, is attached to the housing 94 to transfer water into the chamber 102 of the housing 94 to maintain the chamber 102 of the housing 94 in a predetermined humidity of at least 80%. The at least one sprinkler 112, 114 includes a first sprinkler 112, disposed in the chamber 102, attached to the top wall 96 of the housing 94 and a second sprinkler 114, disposed in the chamber 102 and opposite of the first sprinkler 112, attached to the bottom wall 98 of the housing 94. The bottom wall 98 of the housing 94 further defines a drain 116 disposed adjacent to the side wall 100 of the housing 94 to remove excess water from the chamber 102 of the housing 94. A heater 118 is disposed in the housing 94 of the chamber 102 and attached to the top wall 96 of the housing 94 to maintain the chamber 102 of the housing 94 at a predetermined temperature of between 70° F. and 80° F. The top wall 96 of the housing 94 defines an exit 120 disposed adjacent to the side wall 100 of the housing 94 for removing the purified air from the chamber 102 of the housing 94.

The mixture of woodchips of the filter media 110 including a plurality of hardwood chips being present between 30 wt. % and 50 wt. %, more preferably 50 wt. %, and a plurality of softwood chips being present between 50 wt. % and 70 wt. %, more preferably 50 wt. %. The filter media 110 further includes a plurality of microorganisms disposed therein for removing odor from the odorous air.

It is another aspect of the present invention to provide a method for breaking down a pallet including plastic, paper, cardboard, and organic material to produce bio-gas, fertilizer, and water. The method utilizes an apparatus including a conveyor 70, a shredder 44, a compactor, and a separator 84. The method also uses an anaerobic digester and a biofilter 92. The biofilter 92 has a housing 94 defining a chamber 102. The housing 94 has at least one entrance 104, 106 and a drain 116 disposed in communication with the chamber 102. The housing 94 also includes at least one sprinkler 112, 114, a heater 118, and a plurality of trays 108 including a filter media 110.

Figure 6:
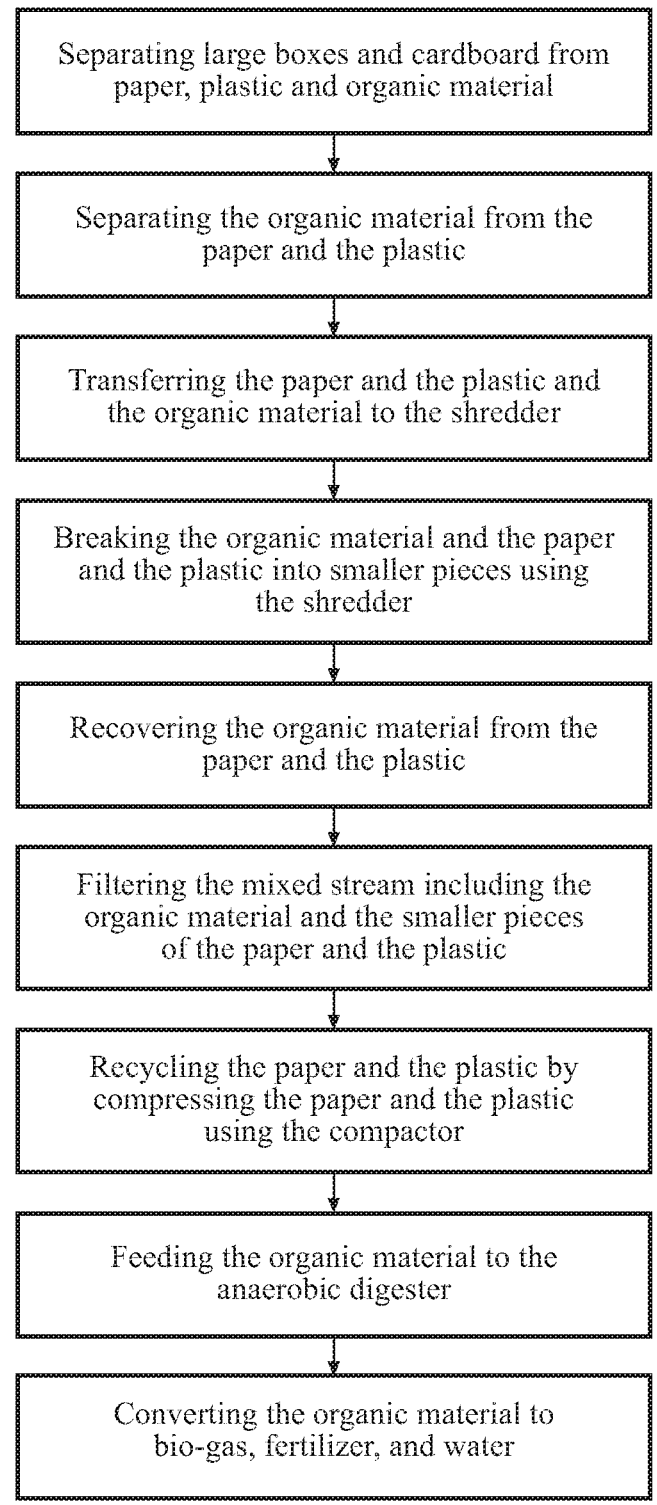
FIG. 6 is a schematic flowchart of the method for separating a pallet including plastic, paper, cardboard, and organic material, and converting the organic material to bio-gas, fertilizer, and water.

As best show in FIG. 6, the method includes a first step of removing the cardboard from the paper, the plastic, and the organic material. The next step of the method is separating the organic material from the paper and the plastic. The step of separating includes a step of transferring the paper, the plastic, and the organic material to the shredder 44. The paper, the plastic, and the organic material may be transferred to the shredder 44 either manually or using a conveyor 70 belt. The step of separating also includes a step of breaking the organic material, the paper, and the plastic into smaller pieces using the shredder 44. In addition, the step of separating further includes a step of recovering the organic material from the paper and the plastic by adding water to the shredder 44 during the step of breaking the organic material, the paper, and the plastic to produce a mixed stream including the organic material and smaller pieces of the paper and the plastic. The step of separating further includes a step of filtering the mixed stream including the organic material and the smaller pieces of the paper and the plastic through the separator 84 to remove the smaller pieces of the paper and the plastic from the mixed stream.

The next step of the method is recycling the paper and the plastic. The step of recycling the paper and the plastic may be performed by compressing the paper and the plastic using the compactor and delivering the compressed paper and plastic to a recycling station. At the same time or soon after, the organic material is fed to the anaerobic digester. The next step of the method is converting the organic material to the bio-gas, the fertilizer, and the water using the anaerobic digester.

Figure 7:
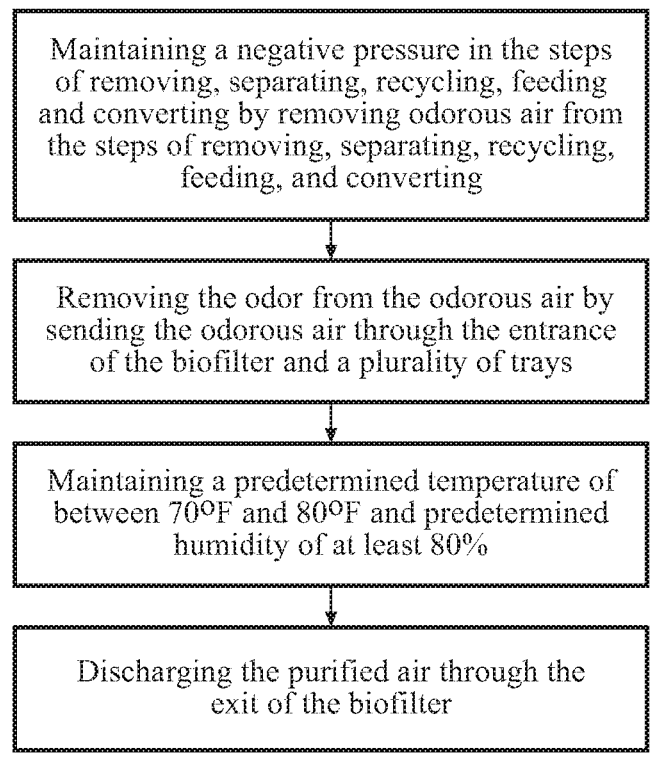
FIG. 7 is a schematic flowchart of the process of removing odorous air.

As best shown in FIG. 7, throughout the steps of removing, separating, recycling, feeding and converting a negative pressure maintained to clean the odorous air generated during the steps of removing, separating, recycling, feeding, and converting. The step of maintaining the negative pressure is further defined as removing odorous air generated during the steps of removing, separating, recycling, feeding, and converting. The step of removing odorous air further includes a step of feeding the odorous air through the entrance of the biofilter 92 and through the plurality of trays 108 including the filter media 110 in the chamber 102 of the biofilter 92 to eliminate odor and produce purified air. The step of removing odor further includes a step of maintaining a predetermined temperature, preferably between 70° F. and 90° F., in the chamber 102 of the biofilter 92 using the heater 118. The step of removing odor also includes a step of maintaining a predetermined humidity, preferably of at least 80%, in the chamber 102 of the biofilter 92 using the plurality of sprinklers 112, 114. The step of removing odor further includes a step of discharging the purified air through the outlet 68 of the biofilter 92.

Obviously, many modifications and variations of the present invention are possible in light of the above teachings and may be practiced otherwise than as specifically described while within the scope of the appended claims. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims.

What is claimed is:

1. A method for breaking down a pallet, removing odorous air, and producing bio-gas, fertilizer, and water using an anaerobic digester and a biofilter, the pallet including plastic, paper, cardboard, and organic material, and the biofilter having a housing defining a chamber, the housing chamber having at least one entrance, a drain, at least one sprinkler, a heater, and a plurality of trays including a filter media having a plurality of microorganisms, said method comprising the steps of:

removing the cardboard from the paper and the plastic and the organic material;

separating the organic material from the paper and the plastic;

recycling the paper and the plastic;

feeding the organic material to the anaerobic digester;

converting the organic material to the bio-gas and the fertilizer and the water using the anaerobic digester; and removing odorous air generated during said step of separating, said step of recycling, said step of feeding, and said step of converting by maintaining a negative pressure during said step of removing the cardboard, said step of separating, said step of recycling, said step of feeding and said step of converting;

said step of removing the odorous air further including feeding the odorous air through the entrance of the chamber of the biofilter and through the plurality of trays including the filter media, the filter media further having a mixture of a plurality of hardwood chips and a plurality of softwood chips, to eliminate odor and produce purified air from the odorous air;

said step of removing the odorous air further including a step of maintaining a predetermined temperature of between 70° F. and 80° F. in the chamber of the biofilter;

wherein each of the trays is an open tray containing the filter media and the at least one sprinkler includes a plurality of sprinklers whereby each of the sprinklers is located above each of the trays;

said step of removing the odorous air further including a step of maintaining a predetermined humidity of at least 80% in the chamber of the biofilter to eliminate the odor from the odorous air.

2. The method as set forth in claim 1 wherein said step of removing the odorous air further includes a step of discharging the purified air through an outlet of the biofilter.

* * * * *